United States Patent [19]

Sulc et al.

[11] Patent Number: 4,946,470
[45] Date of Patent: Aug. 7, 1990

[54] HARD INTRAOCULAR LENS WITH THE SHAPE MEMORY

[75] Inventors: Jiří Šulc; Zuzana Krčová, both of Prague, Czechoslovakia

[73] Assignee: Ceskoslovenska akademie ved, Prague, Czechoslovakia

[21] Appl. No.: 331,503

[22] Filed: Mar. 31, 1989

[30] Foreign Application Priority Data

Apr. 1, 1988 [CS] Czechoslovakia .................. 2261-88

[51] Int. Cl.$^5$ .............................................. A61F 2/16
[52] U.S. Cl. ....................................... 623/6; 523/106; 525/937
[58] Field of Search .................. 523/106; 525/937; 623/6; 526/328.5

[56] References Cited

U.S. PATENT DOCUMENTS 4,384,097  5/1983  Wingler et al. .................. 526/328.5
4,578,504  3/1986  Hammar .......................... 560/112
4,731,079  3/1988  Stoy ................................ 623/6

Primary Examiner—Ronald Frinks
Attorney, Agent, or Firm—Leydig, Voit & Mayer

[57] ABSTRACT

A hard introcular lens having shape memory consisting of a copolymer having a glass transition temperature ($T_g$) from 40° C. to 60° C. that is deformable into the shape of a straight or bent rod with a diameter of 1 to 4 mm at a temperature above its $T_g$ temperature and cooled to fix the deformation for insertion into the human eye through a small incision. After insertion into the eye the deformed lens will soften and relax to its original undeformed shape by elevating its temperature with a rinsing solution above 40° C. and will maintain its final shape after a subsequent temperature reduction at normal body temperature of about 37° C. whereby the lens becomes a hardened lens.

1 Claim, No Drawings

HARD INTRAOCULAR LENS WITH THE SHAPE MEMORY

The invention relates to a hard intraocular lens with the shape memory, which is able to replace the natural eye lens and is determined for insertion inside an eye, i.e. into the anterior or posterior chamber or closely under cornea.

The lenses used so far for this purpose have a definite shape and physical state already before their operational insertion into eye. These lenses are made either from hard polymers of esters of methacrylic or acrylic acid with lower aliphatic alcohols, e.g. methyl methacrylate (MMA), or from soft hydrogels swelled in physiological saline to equilibrium before insertion into eye. A relatively long incision is necessary in both cases in order to insert the lens into its place. The hard lenses cannot be deformed at all at applicable temperature and thus the insertion cannot be facilitated, while the possible temporary deformation is either limited or excluded with common hydrogel lenses from lightly crosslinked polymers, as is the polymer of hydroxyethyl methacrylate (HEMA), due to their liability to break at too sharp bending. However, the hard lenses increase the risk of injury of sensitive eye tissues during insertion to the place.

A substantial improvment represents the intraocular lens which is before and during operation in the effectively deformed state enabling to reduce the incision to minimum and which acquires the definite shape in the correct position in eye according to the U.S. patent application Ser. No. 134,222 filed Dec. 17, 1987, now Pat. No. 4,834,753.

The purposeful deformation is, for example, coiling or compression of the lens into a narrow rod or, at least, its simple or multiple folding or rolling, in order to shorten the necessary length of incision at least to a half.

This lens is swelled prior to operation in a swelling agent to such extent that its glass-transition temperature is between −5° C. and 45° C. The lens containing a reduced amount of swelling agent, so that its $T_g$ is in the above given region, is deformed in the relaxed state into the shape suitable for operation, for example, by coiling from both sides, and cooled below $T_g$ to fix this deformation.

After operation, which is considerably facilitated by this deformation, the lens relaxes in eye by postswelling during heating to the temperature of eye and in this way acquires the desirable original shape, elasticity and softness.

The rapidity of decoiling is predetermined and the surgeon has to work very quickly, with skill, and must not make a mistake. Moreover, the intraocular lens which floats in body liquid responses to vibrations. A soft intraocular lens is more subjected to such vibrations and transfers them to haptics supporting the intraocular lens by leaning against the fibrous apparatus of eye. This stresses the tissue in the place of contact and may cause its gradual atrophy. Deformation of the optical part and defocusing of the optics may also occur as a consequence of vibrations of soft elastic intraocular lenses.

These shortcomings are overcome in a hard intraocular lens with the shape memory according to the present invention.

The substance of the hard intraocular lens with shape memory according to the invention is that the lens consists of a copolymer having the glass-transition temperature $T_g$ in the region from 40° to 60° C.

Another feature of this hard hydrophilic intraocular lens is that it is deformed into the shape suitable for operation. advantageously into a straight or bent rod with diameter 1 to 4 mm.

In the case of the intraocular lens according to the invention, the copolymers of methyl methacrylate with butyl methacrylate, 2-hydroxyethylmethacrylate with methyl methacrylate, methyl methacrylate with methacrylamide, and the like, may be used, where, as the ratio of individual monomers is chosen in such a way that the glass-transition temperature is in the above given region.

The lens having the given $T_g$ is heated about 50° C., deformed at this temperature, and cooled to fix the deformation. The lens deformed in this way remains in the deformed state after operation until the eye begins to be rinsed with an irrigation solution of temperature above 40° C. First then it starts to decoil into its final shape and hardens again after the temperature decreases to 37° C.

This hard intraocular lens is not affected by vibrations in eye and a defocusing of optics does not occur. The hard intraocular lens according to the invention combines the advantage of soft intraocular lenses with respect to the possible deformation for the purpose of operation and of hard intraocular lenses, for example, from methyl methacrylate, with respect to the behavior in eye.

The invention is further illustrated in the example without limiting its scope.

EXAMPLE

A mixture of 40 wt. parts of methyl methacrylate and 60 wt. parts of 2-hydroxyethyl methacrylate (HEMA) was placed in an ampoule, 0.05% of azo-bis-isobutyronitrile was added, the ampoule was bubbled through with argon and sealed. Then it was heated in a water bath to 60° C. for 48 hours and to 80° C. for further 24 hours. An intraocular lens was made by turning from a plug removed from the ampoule. The lens was swelled in physiological saline, deformed at 50° C. into a rod-like shape with diameter 2 mm, and cooled down. It was inserted into an eye through a small 3-mm incision. After elevating the temperature by rinsing with a solution heated to 48° C., the lens softened and aquired its original shape. After temperature decreased to 37° C., i.e. to the human body temperature, the lens hardened and behaved as the lens from poly(methyl methacrylate) (PMMA).

What is claimed is:
1. A hard intraocular lens having a shape memory
   (1) that is made of a copolymer which has a glass transition temperature ($T_g$) from about 40 to about 60 degrees C. and has an original shape suitable for functioning as an intraocular lens after implantation in a human eye;
   (2) that is capable of being deformed, at a temperature above its $T_g$, into the shape of a rod which has diameter from about 1 to 4 mm and which is capable of being inserted into the human eye;
   (3) that will soften and relax to its original shape upon being rinsed in the eye with a rinsing solution having a temperature from about 40 degrees to about 50 degrees C.; and
   (4) that will harden and remain hardened at normal body temperature of about 37 degrees C.

* * * * *